United States Patent
Chang et al.

(10) Patent No.: US 10,302,524 B2
(45) Date of Patent: May 28, 2019

(54) DETECTION AND ASSESSMENT OF DAMAGE TO COMPOSITE STRUCTURE

(71) Applicant: The Boeing Company, Chicago, IL (US)

(72) Inventors: Li Chun Chang, Mt. Pleasant, SC (US); James M. Fortier, Renton, WA (US); Ronald J. Steckman, Carleston, SC (US); Richard M. Coleman, Renton, WA (US)

(73) Assignee: The Boeing Company, Chicago, IL (US)

( * ) Notice: Subject to any disclaimer, the term of this patent is extended or adjusted under 35 U.S.C. 154(b) by 105 days.

(21) Appl. No.: 15/458,569

(22) Filed: Mar. 14, 2017

(65) Prior Publication Data

US 2017/0184650 A1    Jun. 29, 2017

Related U.S. Application Data

(63) Continuation of application No. 14/171,943, filed on Feb. 4, 2014, now abandoned.
(Continued)

(51) Int. Cl.
*G01M 5/00* (2006.01)
*B64D 45/00* (2006.01)
(Continued)

(52) U.S. Cl.
CPC .......... *G01M 5/0016* (2013.01); *B29C 73/10* (2013.01); *B64D 45/00* (2013.01); *B64F 5/40* (2017.01);
(Continued)

(58) Field of Classification Search
CPC ..................... B64D 2045/0085; G01M 5/0016
See application file for complete search history.

(56) References Cited

U.S. PATENT DOCUMENTS

| 4,145,915 A | 3/1979 | Oertle |
| 5,015,950 A | 5/1991 | Rose et al. |

(Continued)

FOREIGN PATENT DOCUMENTS

WO    2012010496 A1    1/2012

OTHER PUBLICATIONS

Baker et al., "Towards a practical structural health monitoring technology for patched cracks in aircraft structure", Composites Part A: Applied Science and Manufacturing, Elsevier Science Publishers B.V., Amsterdam, NL, vol. 40, No. 9, Sep. 1, 2009, pp. 1340-1352.
(Continued)

*Primary Examiner* — Jennifer E Simmons
(74) *Attorney, Agent, or Firm* — Miller, Matthias & Hull LLP

(57) ABSTRACT

Methods and systems for monitoring an integrity of electrical connectivity between a repair patch and a parent structure include providing the repair patch with an embedded sensor configured to detect electrical conductivity. The repair patch includes a ply of conductive material that overlaps a portion of a conductive layer of the parent structure. A baseline set of sensor data is acquired from the sensor indicative of an electrical connectivity between the ply of conductive material of the repair patch and the conductive layer of the parent structure. One or more additional sets of data may be obtained from the sensor and compared to the baseline set of data to determine an integrity of the electrical connectivity between the ply of conductive material of the repair patch and the conductive layer of the parent structure.

20 Claims, 9 Drawing Sheets

Related U.S. Application Data

(60) Provisional application No. 61/920,808, filed on Dec. 26, 2013.

(51) Int. Cl.

| | | |
|---|---|---|
| *G01N 3/02* | (2006.01) | |
| *G01N 3/06* | (2006.01) | |
| *B64F 5/60* | (2017.01) | |
| *B64F 5/40* | (2017.01) | |
| *G01N 27/20* | (2006.01) | |
| *G01R 31/02* | (2006.01) | |
| *G07C 5/00* | (2006.01) | |
| *B29C 73/10* | (2006.01) | |

(52) U.S. Cl.
CPC ............ *B64F 5/60* (2017.01); *G01M 5/0033* (2013.01); *G01M 5/0083* (2013.01); *G01M 5/0091* (2013.01); *G01N 3/02* (2013.01); *G01N 3/066* (2013.01); *G01N 3/068* (2013.01); *G01N 27/20* (2013.01); *G01R 31/02* (2013.01); *G07C 5/006* (2013.01); *B64D 2045/0085* (2013.01)

(56) References Cited

U.S. PATENT DOCUMENTS

| | | |
|---|---|---|
| 5,195,046 A | 3/1993 | Gerardi et al. |
| 5,814,729 A | 9/1998 | Wu et al. |
| 6,006,163 A | 12/1999 | Lichtenwalner et al. |
| 6,370,964 B1 | 4/2002 | Chang et al. |
| 6,399,939 B1 | 6/2002 | Sundaresan et al. |
| 6,768,312 B2 | 7/2004 | Sun et al. |
| 7,302,866 B1 | 12/2007 | Malkin et al. |
| 7,898,246 B2 | 3/2011 | Georgeson et al. |
| 8,186,223 B2 | 5/2012 | Dawson et al. |
| 2009/0033323 A1 | 2/2009 | Georgeson et al. |
| 2009/0129431 A1* | 5/2009 | Safai ............ G01N 25/72 374/45 |
| 2009/0157358 A1 | 6/2009 | Kim |
| 2009/0259411 A1 | 10/2009 | Loomis et al. |
| 2010/0132875 A1* | 6/2010 | Ackerman .......... B29C 73/10 156/98 |
| 2011/0135474 A1 | 6/2011 | Thulke et al. |
| 2011/0316712 A1 | 12/2011 | McIver et al. |
| 2013/0192381 A1 | 8/2013 | Becker et al. |
| 2015/0344156 A1* | 12/2015 | Vail, III ............ B64F 5/60 701/32.8 |

OTHER PUBLICATIONS

Takeda et al., "Debonding monitoring of composite repair patches using embedded small-diameter FBG sensors", Smart Materials and Structures, IOP Publishing Ltd., Bristol, GB, vol. 16, No. 3, Jun. 1, 2007, pp. 763-770.

European Examination Report dated Aug. 19, 2016, European Application No. 14191516.5 (European Counterpart of the parent of the instant U.S. patent application).

European Examination report dated Feb. 16, 2016, European Application No. 14191516.5 (European Counterpart of the parent of the instant U.S. patent application).

Ihn et al., "Detection and monitoring of hidden fatigue crack growth using a built-in piezo electric sensor/actuator network: II. Validation using rivited joints and repair patches", Smart Mater. Struct. 13 (2004) 621-630.

Wu et al., "Health monitoring of bonded composite repair in bridge rehabilitation", Smart Mater. Struct. 17 (2008) 045014, 9pp.

Loewke et al., "Structural Health Monitoring of Composite Materials Using the Two Dimensional Fast Fourier Transform", 2004, found at: https://www.semanticscholar.org/paper/Structural-Health-Monitoring-of-Composite-Loewke-Meyer/43f763a94ca8969f05226d535ed9fa95977aebed.

Office Action for related Singapore Application No. 10201408647W; Report dated Oct. 30, 2017.

Quing X. P. et al., A real-time active smart patch system for monitoring the integrity of bonded repair on an aircraft structure. Smart Mater. Struct., May 9, 2006, vol. 15, No. 3, pp. N66-N73, abstract; p. N67 left column, second paragraph; p. N67 right column, 2. System principles. first paragraph; p. N68 left column, first and third paragraphs; p. N68 right column, first paragraph; p. N71 right column, first and second paragraphs; figure 2. Citation is not enclosed due to copyright restrictions.

Baker A., et al., Towards a practical structural health monitoring technology for patched cracks in aircraft structure. Composite Part A: Applied Science and Manufacturing, Sep. 30, 2008, vol. 40, No. 9, pp. 1340-1352 abstract, p. 1341:2. Basic requirements of a SHM system, first and second pragraphs; figure 1. Citation is not enclosed due to copyright restrictions.

Takeda S., et al., Debonding monitoring of composite repair patches using embedded small-diameter FBG sensors. Smart Mater. Struct., Apr. 24, 2007, vol. 16, No. 3, pp. 763-770 abstract, p. 763:1. Introduction, first and second paragraphs. Citation is not enclosed due to copyright restrictions.

Office Action for related Chinese Application No. 201410833818.1; Report dated Apr. 28, 2018.

Office Action for related GCC Application No. 2014-28634; Report dated Jun. 6, 2018.

* cited by examiner

DETECTION AND ASSESSMENT OF DAMAGE TO COMPOSITE STRUCTURE

CROSS-REFERENCE TO RELATED PATENT APPLICATIONS

This application is a continuation of U.S. application Ser. No. 14/171,943, filed on Feb. 4, 2014, which in turn claims the benefit, under Title 35, United States Code, § 119(e), of U.S. Provisional Application No. 61/920,808 filed on Dec. 26, 2013, the disclosures of which are incorporated by reference herein in its entirety.

BACKGROUND

This disclosure generally relates to systems and methods for detecting and assessing damage to composite structure. This process and method is compatible with but not limited to composite structures that use lightning protection systems.

Modern aircraft are being designed and built with greater percentages of composite materials. In some aircraft, more than 50% of the structural components are being manufactured with composite materials. Composite materials are tough, lightweight materials. Dominating types of composite materials, such as glass fibers, carbon fibers, aramid fibers or boron fibers, are combined with a coupling agent such as a resin, to create a product with improved or exceptional structural properties not present in the original materials. Composite materials are lighter and have better mechanical and fatigue properties as compared to aluminum. However they are also less electrically conductive and provide less electromagnetic shielding. Reduced conductivity causes reduced current dissipation which may result in damage when an electromagnetic effect, such as a lightning strike, occurs.

Specifically, when lightning hits an aircraft, a conductive path on the skin of the aircraft allows the electricity to travel along the skin and exit at some other location on the aircraft. Without an adequate conductive path, arcing and hot spots can occur, possibly affecting the skin. Also, the lower electrical shielding capability of composite materials increases the lightning threat to wiring and systems within the aircraft.

One current mechanism used to protect composite skins on aircraft against lightning strike damage is to include conductive lightning skin protection systems. Such systems may be present either in or on the composite skins of an aircraft. One type of system used to provide a conductive path on the aircraft is an interwoven wire fabric (IWWF). With this type of system, wires, such as phosphor-bronze wires are embedded in the top layer of the composite material nearest the wind-swept surface. Other types of systems may include the use of a thin copper foil. With an interwoven wire fabric system in the fuselage, the wires typically have a thickness range of about 0.003 to about 0.004 inches. These types of wires are spaced apart from each other. A typical spacing is around 0.010 inch in a 90-deg mesh pattern.

High-intensity electrical discharges, such as lightning strikes to a composite material including IWWF, may result in non-compliant properties of the IWWF within the composite material, which in turn results in a portion of the composite material that is non-compliant. Certain portions of the non-compliant composite material may not be identifiable by sight. The non-compliant IWWF must be replaced to provide electromagnetic event (EME) protection for the aircraft, including removing areas with IWWF loss and replacing the removed areas with compliant IWWF.

In addition, testing has shown that certain lightning protective structures tend to experience substrate microcracking and finish cracking. The microcracks tend to form due to repeated and extreme temperature, humidity, and pressure fluctuations. Microcracking occurs due to a number of factors including internal stresses from differences in coefficient of thermal expansion, as well as from non-optimum interface adhesion between components in composite systems.

Fiber-reinforced composite skin panels may require a localized repair to remove a portion of the panel that has been compromised. The localized repair includes removing the compromised portion of the panel, preparing the area to be repaired, generally sanding surrounding composite and edge portions in a ramped or stepped manner, fabricating, bonding and curing a composite patch that employs sufficient overlap of the composite material and interwoven wire fabric to ensure the transfer of energy from a lightning strike on the bonded repair section into the surrounding skin panel.

Different methodologies are currently being used to inspect repaired structures made of composite material. For example, U.S. Pat. No. 7,898,246 discloses a method for non-destructive inspection of a repaired composite structure comprising interwoven wire fabric. Existing processes are used to validate structural repairs, but do not validate interwoven wire fabric conductivity. In particular, they neither detect the need for maintenance or repair of interwoven wire fabric damage nor isolate or assess potential risk for EME/HIRF-related issues.

Any improvement upon the state of the art for systems and methods for inspecting and/or monitoring the health of a composite structure would be beneficial, especially if such improvement could be applied to both original and repaired composite structure.

SUMMARY

The subject matter disclosed herein is directed to systems, processes and software algorithms designed to provide prognostic information and to locate and identify, assess severity, and verify maintenance and repair of composite structure. The systems disclosed herein provide routine information for maintenance and repair personnel and enable damage assessments to support dispatch in the event of structural or embedded systems damage, e.g., manufacturing process impurities, repair failure, or composite material that has been over-strained, cut, burnt, delaminated, etc.

Some processes disclosed herein provide integrated measurement and test techniques to maintain composite structure comprised of interwoven wire fabric health throughout an airplane life cycle and to detect the occurrence of a level of damage that could potentially lead to EME/HIRF (High-Intensity Radiated Field) related issues. In particular, the systems disclosed herein are able to identify possible disturbances of conductivities and/or delaminations in existing composite structure and newly introduced composite structure due to repair to protect internal systems from EME/HIRF-related system damage. The information acquired by the system can be used to assess the severity of dynamic impacts, such as those due to shockwaves or lightning strikes.

In accordance with illustrative embodiments disclosed herein, a system and a methodology are provided for monitoring the structural integrity of a composite structure with respect to an area that has been repaired. When composite structure is repaired, there are also electrical considerations, due to lightning strike concerns, that are satisfied by ensuring overlap of the interwoven wire fabric during patch preparation. Illustrative embodiments disclosed below employ embedded sensors, radio-frequency identification (RFID), and data extraction. In particular, some of the systems disclosed herein enable life cycle monitoring of included lightning strike mitigation devices in composite repair areas.

The composite repair systems disclosed herein comprise a sensor (sensor types may include pressure, strain (e.g., strain gage), electrical conductivity, fiber optic, acoustical, and capacitive) which is embedded between plies of a composite repair patch. Each repair patch on an aircraft can be provided with one or more sensors. In some instances, a plurality of discrete sensors are arranged at selected locations in a repair patch. In other instances, a sensor can be specifically designed to have a shape that conforms to the shape of the repair patch.

After the composite repair has been cured, the outputs of the sensor or sensors embedded in the repair site are monitored. The sensor output signals are then processed to identify acquired data sets indicating the possible presence of structural damage to the repair site. In accordance with some embodiments, the measured values output by a sensor after the repair has been completed and before the repaired parent structure (e.g., an aircraft) has been returned to service are considered a baseline.

After the repaired parent structure has been returned to service, the integrity of the repair site can be continuously or periodically monitored by acquiring and processing data outputted by the sensor or sensors embedded in the repair patch. During life cycle monitoring, the output of each sensor is compared to a respective baseline value. While environmental conditions during service are a factor (e.g., temperature), the sensor outputs must be processed in a manner that removes the effects attributable to environmental factors which were absent during determination of the baseline values. When the deviation of the monitored sensor output from the baseline sensor output reaches a predefined threshold (which threshold is different for every repair situation), the patch will be repaired or replaced. The monitoring system has the capability to issue an alert or warning signal that causes the production of a visible or audible alert or warning in the cockpit, or storage of data in a memory, in response to detection of a situation wherein the monitored sensor output has deviated from the baseline sensor output by more than a specified threshold.

One aspect of the subject matter disclosed herein a method for monitoring structural integrity of a laminated structure made of composite material. The method comprises: (a) placing a sensor between plies of composite material which are not fully cured, the sensor being capable of outputting data representing a current structural characteristic of surrounding composite material after the composite material has been cured; (b) curing the plies of composite material while the sensor is in place to produce composite material having an embedded sensor; (c) after the curing step, acquiring and recording baseline data from the embedded sensor which represents a structural characteristic of the surrounding composite material; (d) after the baseline data has been acquired and recorded, subjecting the laminated structure to loads having unknown magnitudes and directions; (e) acquiring and recording post-loading data from the embedded sensor at a time subsequent to or during step (d), the post-loading data representing a structural characteristic of the surrounding composite material; (f) processing the baseline data and post-loading data in a manner that identifies differences between the respective baseline and post-loading data indicative of structural change in the surrounding composite material; and (g) determining whether the identified differences indicate structural change to the surrounding composite material in excess of a specified threshold. The steps (e) through (g) are performed by a computer system. In some embodiments, step (f) comprises creating a baseline signature based on the baseline sensor data, creating a post-loading signature based on the post-loading sensor data, and comparing the baseline and post-loading signatures.

The foregoing method may further comprise: issuing an alert signal in response to a determination in step (g) that the identified differences indicate structural change to the surrounding composite material in excess of a specified threshold; and/or processing the post-loading data to compensate for effects due to differences in local conditions at or about the times when steps (c) and (e) were performed.

In instances where the laminated structure comprises a parent structure having a repair site and a repair patch bonded to the repair site, the method may further comprise: evaluating a current repair dispatch status of the repair based on the results of steps (e) through (g); and specifying an updated maintenance schedule that takes into account the current repair dispatch status.

In accordance with a further aspect of the foregoing method, steps (a) through (g) are performed for each of a plurality of repairs, and the output from respective sensors comprises respective post-loading data for respective repairs and respective sensor identification data for respective sensors. When the laminated structure is part of an aircraft, that laminated structure will be subjected to loads in step (d) during flight of the aircraft. In the latter case, the method may further comprise communicating the post-loading data from the sensor to a computer system onboard the aircraft, wherein steps (e) through (g) are performed while the aircraft is airborne; and/or communicating the post-loading data from the sensor to a computer system on the ground after the aircraft has landed, wherein steps (e) through (g) are performed on the ground.

Another aspect of the subject matter disclosed herein is a system comprising: a parent structure made of composite material and having a repair site; a repair patch made of composite material, the repair patch being bonded to the parent structure at the repair site; and a sensor embedded in the repair patch. The system may further comprise non-volatile memory and an interface unit embedded in the repair patch and electrically connected to the sensor.

A further aspect is a method for monitoring structural integrity of a laminated structure made of composite material, comprising: (a) placing a sensor between layers of composite material of a repair patch, the sensor being capable of outputting data representing a current structural characteristic of surrounding composite material after the composite material has been cured; (b) curing the composite material while the repair patch is in contact with a repair site of a parent structure made of composite material to produce a repaired parent structure having an embedded sensor; (c) after the curing step, acquiring and recording baseline data from the embedded sensor which represents a structural characteristic of the surrounding composite material; (d) after the baseline data has been acquired and recorded, subjecting the repaired parent structure to loads having unknown magnitudes and directions; (e) acquiring and recording post-loading data from the embedded sensor at a time subsequent to or during step (d), the post-loading data representing a structural characteristic of the surrounding composite material; (f) processing the baseline data and post-loading data in a manner that identifies differences between the respective baseline and post-loading data indicative of structural change in the surrounding composite material; and (g) determining whether the identified differences indicate structural change to the surrounding composite material in excess of a specified threshold. Steps (e) through (g) are performed by a computer system.

Yet another aspect is a method for monitoring structural integrity of a repaired component of an aircraft, comprising: (a) placing a multiplicity of plies of repair composite material over a repair site on the component with a sensor disposed between two plies; (b) curing the plies of repair composite material so that the repair composite material, with the sensor embedded therein, is bonded to the repair site; (c) acquiring sensor data from the sensor before and during or after a flight of the aircraft; (d) creating a first signature based on the sensor data acquired before the flight; (e) creating a second signature based on the sensor data acquired during or after the flight; (f) comparing the first and second signatures; (g) identifying differences between the first and second signatures indicative of structural change in the repaired aircraft component; and (h) determining whether the identified differences indicate structural change to the repaired aircraft component in excess of a specified threshold. Steps (d) through (h) are performed by a computer system.

Other aspects of systems that monitor the structural integrity of composite parts using embedded sensors are disclosed in detail and claimed below.

BRIEF DESCRIPTION OF THE DRAWINGS

FIG. 2A—damage due to low-energy impact; FIG. 2B—damage due to medium-energy impact; and FIG. 2C—damage due to high-energy impact.

Reference will hereinafter be made to the drawings in which similar elements in different drawings bear the same reference numerals.

DETAILED DESCRIPTION

Various embodiments of systems and methods for monitoring the structural health of repaired composite material on an aircraft will now be described. However, it should be appreciated that the subject matter disclosed herein is not limited in application to repaired composite material, but also can be applied to original composite material, meaning that during fabrication of a composite structure, sensors (sensor types may include pressure, strain (e.g., strain gage), electrical conductivity, fiber optic, acoustical, and capacitive) can be embedded between plies of composite material at strategic locations where structural health monitoring is desirable. Furthermore, the contents disclosed herein are not limited in their application to composite material on aircraft. Instead the contents herein have application to any structure made of composite material that is intended to comply with structural integrity specifications.

Figure 1:
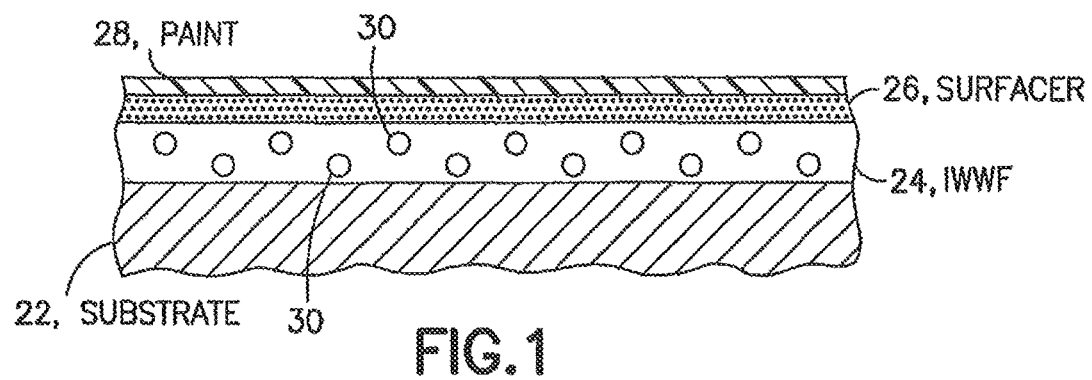
FIG. 1 is a diagram illustrating a cross section of an aircraft skin including interwoven wire fabric.

FIG. 1 is a diagram illustrating a cross section of an aircraft skin including interwoven wire fabric wires. In this example, the depicted structure includes a substrate 22, an interwoven wire fabric (IWWF) layer 24, a surfacer layer 26, and a paint layer 28. The layers above the substrate 22 form an interwoven wire fabric component. Depending on the implementation, the interwoven wire fabric component may only include IWWF layer 24, surfacer layer 26, and paint layer 28. In the alternative, the interwoven wire fabric component may include other layers in addition to or in place of the ones illustrated in this example.

For the purpose of illustration, it will be assumed that the substrate 22 is a composite structure that serves as the skin of a fuselage. Such a composite structure may comprise a laminate made of fiber-reinforced plastic. As seen in FIG. 1, interwoven wire fabric layer 24 contains wires 30, which provide a conductive path for electromagnetic effects, such as a lightning strike. Surfacer layer 26 provides a coating or surface for the application of paint layer 28. The surfacer layer 26 and paint layer 28 form a dielectric component. The dielectric component may include other materials or layers, such as a sealant, a nonconductive primer, or some other combination of those materials along with surfacer layer 26 and paint layer 28. The thickness of the dielectric layer above wires 30 is important because the thickness impacts the dissipation of electrical energy from lightning strikes. As the dielectric thickness increases, greater damage may occur when lightning strikes are encountered. This type of damage is more of an unfavorable issue than a safety issue.

The damage to composite material caused by lightning strikes can be repaired using any one of a number of known methodologies. Many of these known repair techniques involve clean-up of the damaged site followed by the installation of a repair patch made of composite material. For example, U.S. Patent Application Publ. No. 2012/0080135 discloses an in situ repair technique comprising the following steps: (1) remove paint and primer from the defective area using fine abrasive; (2) scarf (i.e., sand) the area around the defect to a depth sufficient to clean out the defective material and to prepare a surface for the repair plies; (3) determine the size, shape and orientation of composite repair plies, make ply templates, and kit plies (the largest repair ply should overlap at least 0.25 inch beyond the periphery of the scarf); (4) apply an adhesive ply to the repair area; (5) compact the adhesive; (6) place a stack of repair plies over the compacted adhesive layer, locating and orienting plies correctly (i.e., in accordance with design specifications) with regard to fiber direction and location tolerance; (7) compact the plies under a pressure of 1 atm; (8) subject the repair site to a soak temperature of 220° F. for a dwell time of 30 minutes without applying pressure to the stack of repair plies; (9) maintaining the soak temperature for another 30 minutes while vacuum pressure is applied to the stack of repair plies; (9) for a patch having 35 plies or less, heat the repair site from the soak temperature to a final cure temperature of 350° F., while maintaining the vacuum pressure on the stack of repair plies, and then hold at that temperature and pressure for 150-180 minutes to achieve full cure; (10) allow the repair site to cool; and (11) perform surface finishing as necessary.

The above-described methodology is suitable for repair of damaged composite material in cases where a hole is not formed and the remaining material at the damaged site can be used as a mandrel for supporting the repair patch. In cases where the composite material is completely removed to form a hole at the damaged site, a different repair methodology will be used involving additional tooling placed on the opposite side of the parent structure.

When repairing composite material that incorporates an IWWF layer 24 (see FIG. 1), the repair patch will also include an IWWF layer. Preferably the repair patch is configured so that the wires of the IWWF layer of the repair patch overlap the wires of the IWWF layer of the parent structure. Nondestructive inspection techniques can be used to determine if bonded repairs on composite panels containing interwoven wire fabrics have a sufficient overlap between the patch material and the parent structure. The overlap width should be sufficient to allow the transfer of energy from a lightning strike on a bonded repair section into the parent material. The overlap width is the width of the edge of the patch material that extends over the undamaged parent material. That width (typically about an inch) is preferably relatively constant all around the patch area.

After the aircraft has been repaired and returned to service, it is preferable that the structural integrity of the repair be monitored at least periodically. Lightning strikes to airplanes may occur without indication to the flight crew. When an airplane is struck by lightning and the strike is evident to the pilot, the pilot must determine whether the flight will continue to its destination or be diverted to an alternate airport for inspection and possible repair. Technicians may find and identify lightning-strike damage by understanding the mechanisms of lightning and its attachment to airplanes. Technicians must be aware that lightning strikes may not be reported in the flight log because the pilots may not have known that a lightning strike occurred on the airplane. Having a basic understanding of lightning strikes will assist technicians in performing effective maintenance. Thus it is desirable to monitor or check an aircraft for damage to composite components caused by lightning strikes at least periodically and preferably continuously.

Figure 2A:
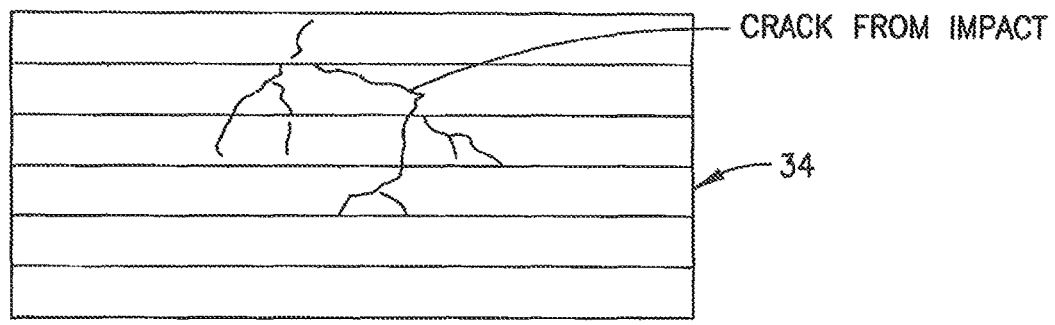
FIGS. 2A-2C are diagrams showing respective types of damage to composite material due to lightning strikes on an aircraft. These diagrams represent cross-sectional views of composite material comprising a lamination of plies of fiber-reinforced fabric in which the fiber orientations differ from ply to ply. The types of damage depicted are as follows.
Figure 2B:
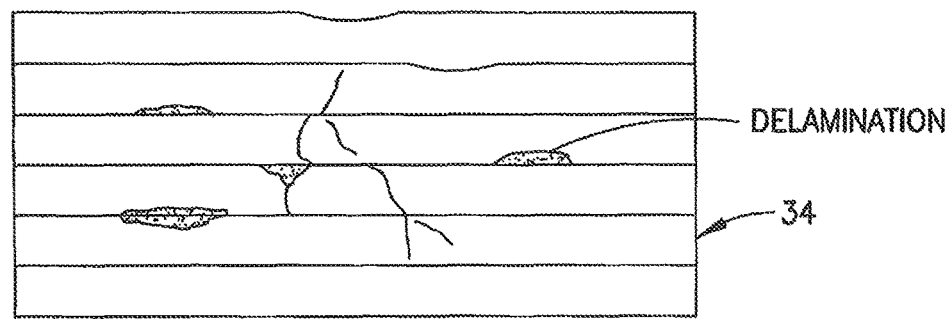
Figure 2C:
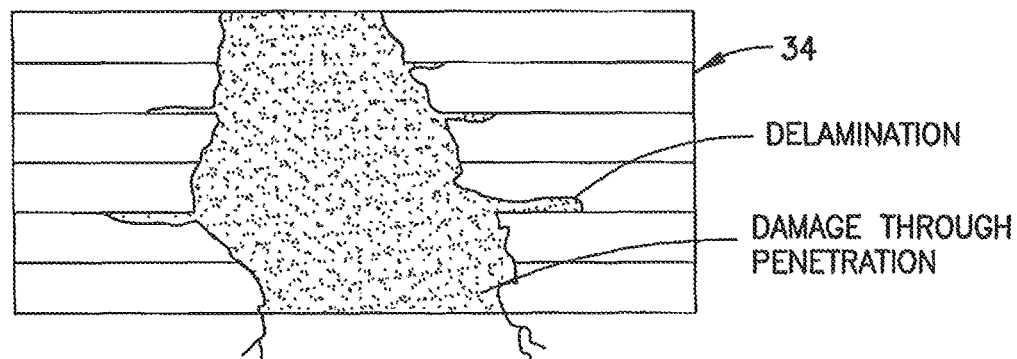

FIGS. 2A-2C are diagrams showing respective types of damage to composite material due to lightning strikes on an aircraft. These diagrams represent cross-sectional views of composite material comprising a lamination of plies of fiber-reinforced polymer in which the fiber orientations (e.g., 0°, ±45°, ±90°) differ from ply to ply. FIG. 2A depicts damage due to low-energy impact in the form of a matrix crack. FIG. 2B depicts damage due to medium-energy impact in the form of local fiber/matrix crushing and delaminations. FIG. 2C depicts damage due to high-energy impact in the form of a through penetration small damage zone, delaminations and loose fiber ends.

Figure 3:
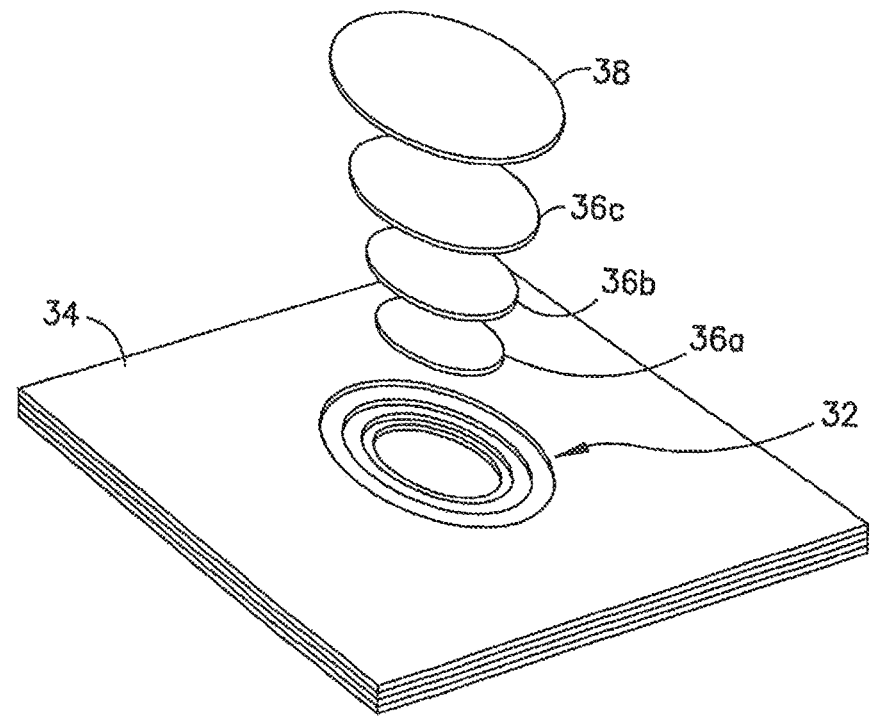
FIG. 3 is a diagram representing an exploded view of a damaged site on a composite parent structure which was repaired using a patch consisting of a multiplicity of (in this simplified example, four) plies of composite material, the outermost ply being IWWF.

FIG. 3 is a diagram representing an exploded view of a damaged site 32 on a composite parent structure 34 which was repaired using a patch consisting of three repair plies 36a-36c of composite material (e.g., carbon or boron fibers embedded in epoxy resin) and an outermost ply of IWWF 38. In a known process, the composite repair plies 36a-36c were fabricated by determining the size, shape and orientation of the composite repair plies 36a-36c, making ply templates, laying composite material on the ply templates, and then curing the composite material. A repair patch having only three plies is shown solely for the purpose of illustrating the concept of a repair patch comprising a multiplicity of plies. The number of plies in a composite repair patch may be far greater than three, for example, a typical repair patch may comprise ten to seventy plies.

In accordance with the systems for monitoring the structural health of repaired composite parts contemplated herein, one or more sensors are embedded between plies of a repair patch. The sensors should have the following characteristics: (1) sensors should be compatible with the composite repair materials when integrated into the repair (i.e., no delaminations, load transfer, chemical damage or electrical incompatibility); (2) sensors should be compatible with the repair process (i.e., able to withstand the pressures and temperatures applied during final cure of the installed repair patch); and (3) sensors should have a sensitivity sufficient to measure the expected parameter (e.g., pressure, stress, strain, electrical conductivity, or "goodness of bond") in the range of aircraft operating environments. In addition, the sensors are designed to support local data storage and wireless and/or wired data acquisition.

Many modern aircraft are provided with a Central Maintenance Computer Function (CMCF). The CMCF encompasses all major avionics, electrical, and mechanical systems installed on the aircraft. The CMCF collects, stores, and displays maintenance information generated by maintenance functionality and installed systems (e.g., member systems-initiated tests). The CMCF has operator interface display and input devices (e.g., multi-purpose control display units (MCDUs)).

The prior art provides airline mechanics with an electronic maintenance terminal display that displays real-time CMCF data screens via Multifunction Control Display Unit (MCDU) emulation. A typical maintenance terminal is a laptop PC comprising a cursor control device, a keyboard, an internal hard drive, a floppy diskette drive, a CD-ROM drive, interfaces for brightness and contrast control, and a graphical output printer bus. Using such a maintenance terminal, authorized personnel are able to access maintenance applications that supervise the aircraft's health status.

Figure 4:
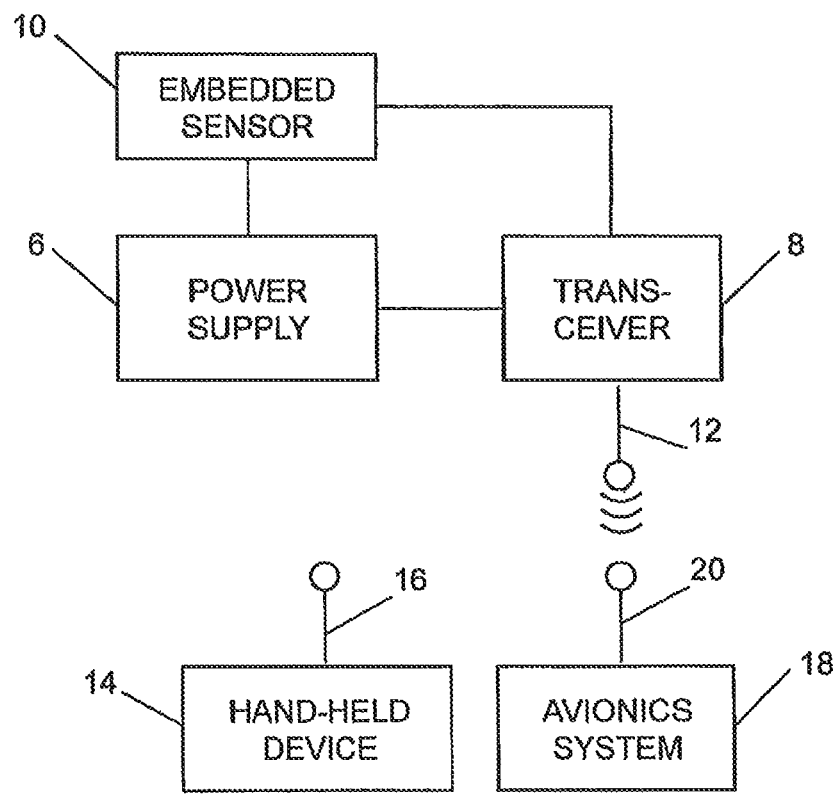
FIG. 4 is a block diagram representing some components of a system for monitoring the structural health of a composite repair in accordance with a wireless embodiment. The sensor can be embedded in a repair patch applied to a repair site.

FIG. 4 identifies some components of a system for monitoring the structural health of a composite repair in accordance with a wireless embodiment. A sensor 10 is embedded in a composite repair patch. The sensor is of a type which transduces the value of a parameter into an electrical output signal, the measured parameter being chosen because its value varies as a function of the degree of post-repair damage incurred by the repair site or the goodness or state of the repair.

In the embodiment depicted in FIG. 4, the embedded sensor 10 receives electrical power from a power supply 6 which is installed at or near the repair site. After appropriate signal conditioning (not shown in FIG. 4) of the output of sensor 10, the conditioned sensor output signal is wirelessly transmitted to either a stand-alone hand-held device 14 having an antenna 16 or an avionics system 18 having an antenna 20 by a transceiver 8 having an antenna 12. The transceiver 8, which also receives electrical power from the power supply 6, may be installed at or near the repair site.

The stand-alone hand-held (i.e., portable) device 14 (e.g., a laptop or tablet) may include functionality typically included in a maintenance terminal as well as the damage detection severity assessment (DDSA) functionality disclosed herein. Current sensor data is recorded by a maintenance technician using the hand-held device 14 when the repaired aircraft is on the ground. That current sensor data will be compared to baseline sensor data to provide an early detection report status. The hand-held device 14 may comprise a processor programmed to compare current sensor data acquired at a time after a flight by the repaired aircraft with baseline sensor data acquired at a time before that flight of the aircraft and then determine whether the differences between the respective sets of sensor data indicate that structural change greater than a specified threshold has occurred in the interim. In the alternative, the hand-held device 14 could download acquired current sensor data to a CMCF or other off-board maintenance computing system with DDSA functionality for processing in a similar manner. The hand-held device 14 may further comprise a display screen for displaying a visual alert when the processor determines that the sensor data is indicative of structural change greater than a specified threshold.

The avionics system 18 may be a component of the onboard CMCF that includes the damage detection severity assessment functionality disclosed herein. In particular, the avionics system 18 may include a software module that monitors the structural integrity of the composite repair over time while the aircraft is airborne and provides early detection of delaminations and/or repair integrity within each repair site. More specifically, the avionics system 18 may comprise a processor programmed to compare current sensor data acquired at a time after a flight by the repaired aircraft with baseline sensor data acquired at a time before that flight of the aircraft and then determine whether the differences between the respective sets of sensor data indicate that structural change greater than a specified threshold has occurred in the interim. In the alternative, the avionics system 18 could download acquired current sensor data to an onboard CMCF for processing in a similar manner. The avionics system 18 may further comprise a flight deck display screen for displaying a sensory alert or maintenance message when the DDSA function determines that the sensor data is indicative of structural change greater than a specified threshold. In addition or in the alternative, the avionics system may comprise an annunciator that issues an audible alert when the processor determines that the sensor data is indicative of structural change greater than a specified threshold.

Sensors can be integrated into the repair at strategic locations based on damage and repair type analysis and depending on sensor type, repair size and criticality. The sensors may be wired (e.g., Ethernet, USB, CANBus) or wireless (e.g., RFID, energy harvesting, WiFi) with local non-volatile memory (NVM) to manage measurement history and status. Discrete sensors as well as sensors in the form of loops and grids, and arrays of discrete sensors are all reasonable sensor configurations. Sensors must be made of materials that integrate into the repair without leaving voids or causing de-bonds, e.g., possibly a tailored and calibrated part of the repair. Sensor types may include pressure, strain (e.g., strain gage), electrical conductivity, fiber optic, acoustical, and capacitive. Some sensors may operate in a current mode, but others may be voltage or even acoustic or optical (e.g., embedded optical fiber may be very compatible with the repair and very sensitive to expected pressure/strain/ "goodness of bond"). Each sensor type has its own type of signal conditioning, power and data acquisition requirements.

The sensors must be compatible with the composite repair materials when integrated (i.e., embedded) into the repair (e.g., no delaminations, allow load transfer, electrically compatible, no chemical damage) and compatible with the repair process (i.e., no pressure and temperature issues during curing of the composite repair materials), while having sufficient sensitivity to measure the expected pressure/stress/"goodness of bond" in the range of airplane operating environments.

In addition, the signal conditioning, power supply and data acquisition functions can be hosted at different locations. For example, circuitry for the signal conditioning, power supply and data acquisition functions can be attached to the repair in a separate interface module, incorporated as part of a stand-alone damage detection severity assessment system; or potentially as part of a standard aircraft interface module (such as a Remote Data Concentrator). Low-power stand-alone applications could depend on power and data acquisition via a wireless RFID type of interface or employ energy harvesting with low-frequency wireless output. Continuous monitored implementations could be powered via energy harvesting or power from vehicle infrastructure and could be wired or wireless.

Figure 5:
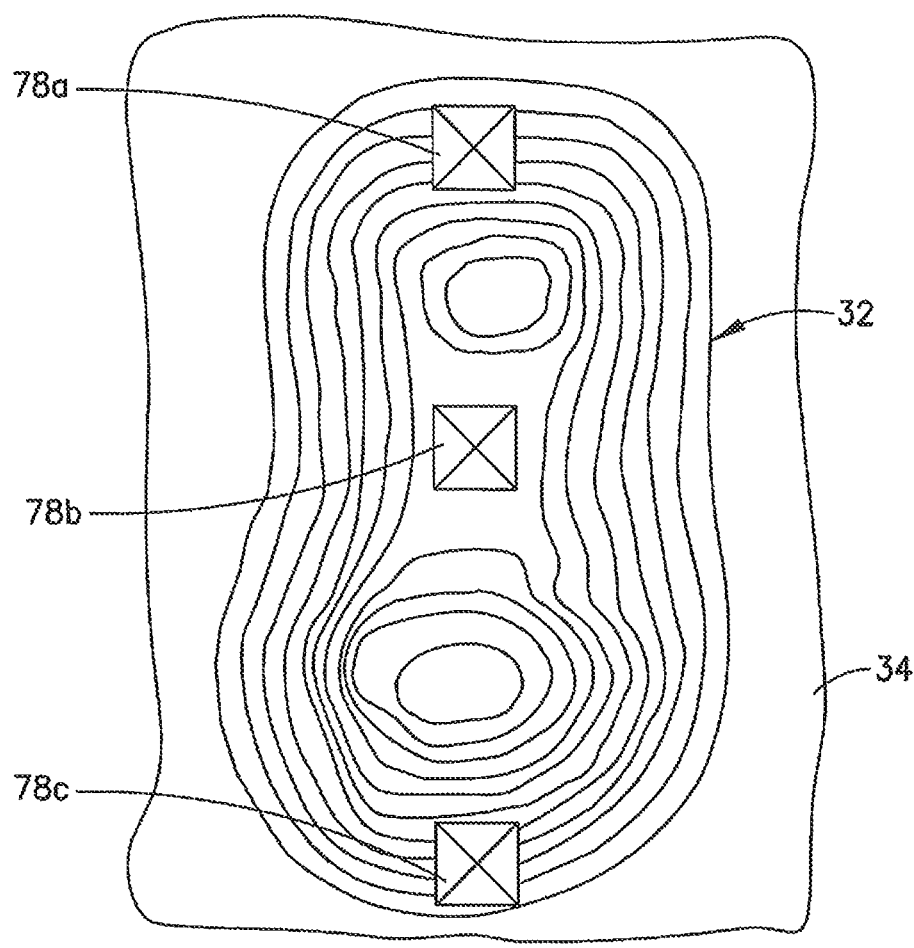
FIG. 5 is a diagram showing a plurality of idealized sensors superimposed on a repair site of a composite parent structure in accordance with one embodiment. The repair patch, in which the sensors will be embedded, is not shown in FIG. 5.

FIG. 5 is an idealized depiction showing respective positions of a plurality of sensor chips 78a, 78b and 78c, each sensor being represented by a respective square having a pair of intersecting internal diagonal lines superimposed on a repair site 32 of a composite parent structure 34 in accordance with one embodiment. The closed contours represent the shapes of respective terraced zones that increase in depth as the zone area decreases. Respective plies of composite material that conform in shape to the respective terraced zones will be laid in place and then bonded to form a repair patch. The repair patch, in which the sensor chips 78a-78c will be embedded, is not shown in FIG. 5. The optimal position and depth of each sensor chip can be determined using stress analysis techniques. Preferably some sensor chips are positioned in areas where the repair is weakest, for example, along a peripheral region in which the repair patch overlies the parent structure. In general, the number of sensors and their locations within the repair will depend on the type and size of the repair and stress analysis.

The sensor chips will be embedded in the composite material with proper grounding and protection to avoid HIRF damage effects.

Figure 6:
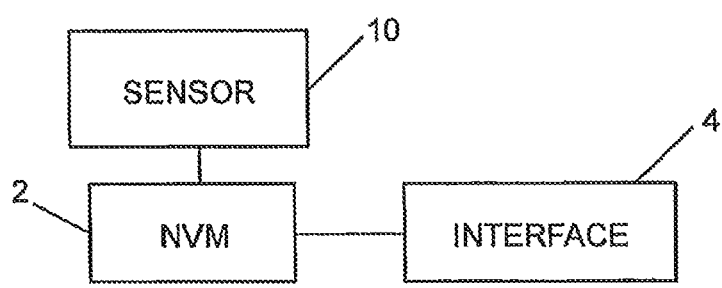
FIG. 6 is a block diagram representing some components of a sensor chip suitable for use in the system depicted in FIG. 5.

In accordance with some embodiments, each embedded sensor chip may be a semiconductor chip (e.g., 3 to 5 mm square) made from materials such as silicon and selenium packed with high-temperature-resistant material. FIG. 6 is a block diagram representing some components of a sensor chip suitable for use in the system depicted in FIG. 5. Each sensor chip comprises a sensor 10, non-volatile memory 2 electrically connected to sensor 10 for local data storage, and an interface unit 4 electrically connected to sensor 10 for wireless or wired data acquisition. The interface unit 4 receives the data output by the sensor 10 and transmits it to a computer system (not shown in FIG. 6) either wirelessly or via a wire (not shown). Each sensor 10 may be fabricated from a material compatible with the composite repair materials and process (e.g., carbon, nanotubes, glass, polymer fiber, silicon, metal foil) or constructed as a microelectromechanical system.

The damage detection severity assessment functionality (which is a software application that runs on a computer system) will now be described with reference to FIGS. 7 and 8.

Figure 7:
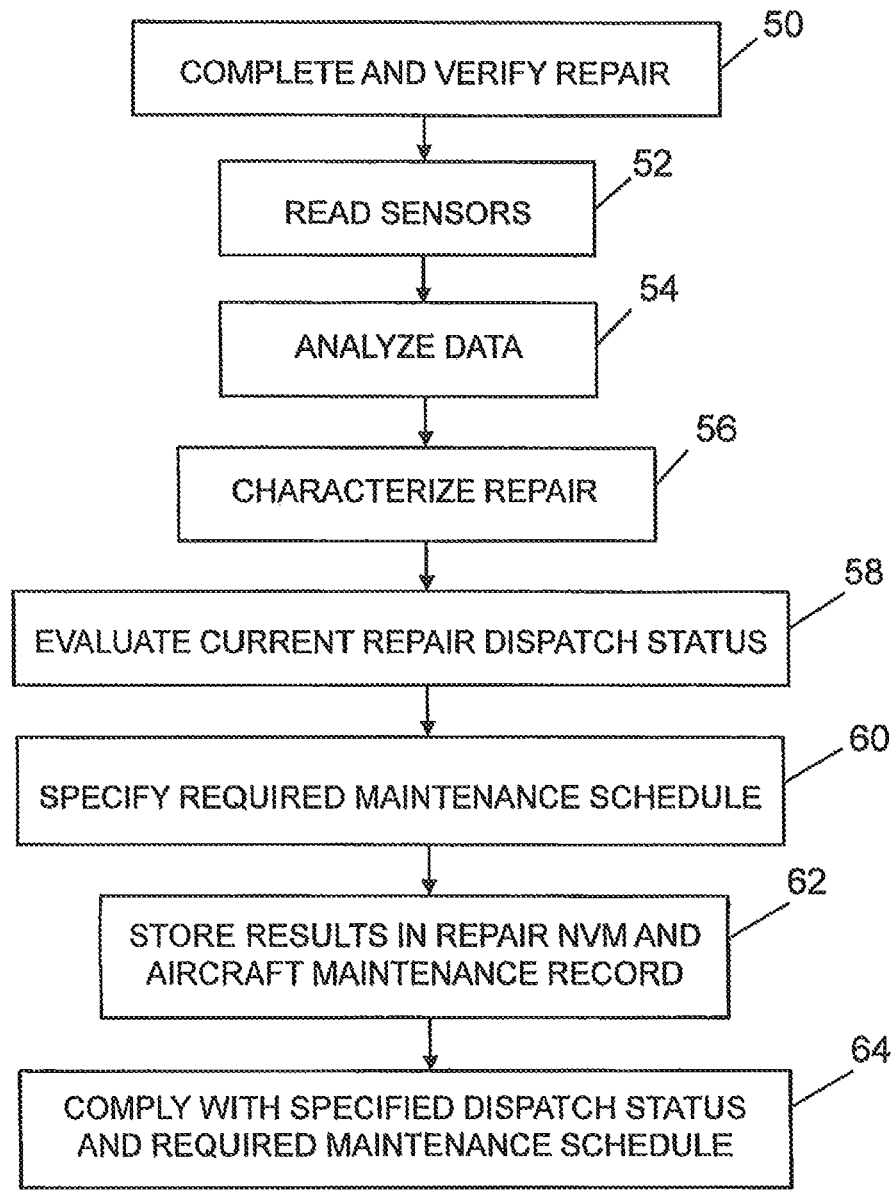
FIG. 7 is a flowchart identifying steps of a process for acquiring information concerning the initial structural integrity of a repair site on a composite structure.

FIG. 7 is a flowchart identifying steps of a process for acquiring information concerning the initial structural integrity of a repair site on an aircraft component made of composite material, i.e., before the aircraft is put back in service. After the repair has been completed and verified (steps 50), the embedded sensors are read (step 52). In the case of wireless communication, the data outputted by the sensors embedded in the completed repair is transmitted to either a stand-alone portable device or an onboard avionics (e.g., CMCF) system, as previously described. In the case of wired communication, the sensor outputs are delivered to output terminals, which in turn are connected by wires to the portable device 14 and/or the avionics system 18. The acquired sensor data is then analyzed (step 54). Analysis and prognostics are used to characterize the repair (step 56). As used herein, "characterization" is the act of creating a unique signature that is a measure of the "repair/bond goodness" of the repair. This signature is the basis for evaluating changes in the repair over time. After the repair has been characterized, the current repair dispatch status is evaluated (step 58). The evaluation of the current repair dispatch status is performed based on the "repair/bond goodness" information and its impact on dispatch of the airplane. The current repair dispatch status might range from "Ready to dispatch" to "Needs maintenance within some number of cycles" to "No Dispatch until maintenance is performed". In light of the state of the repair, i.e., the "repair/bond goodness", a schedule of required maintenance of the particular repair is specified (step 60). All results are stored in a repair non-volatile memory and an aircraft maintenance record (steps 62). Thereafter, the operator of the aircraft complies with the specified dispatch status and the required maintenance schedule (steps 64).

The aircraft operator preferably repeatedly monitors the structural state of the repair for the life of the aircraft in service, complying with the required maintenance schedule. This involves using the damage detection severity assessment software again. Subsequent scheduled uses of the damage detection severity assessment functionality employ the initial characterization of the repair as well as subsequent repair measurement data (and other model-based and empirical repair information) to create an updated signature. With this information, the damage detection severity assessment can determine whether the repair is still structurally sound or not, whether the maintenance schedule needs to be changed and in some cases that the repair is in need of immediate maintenance before dispatch.

Figure 8:
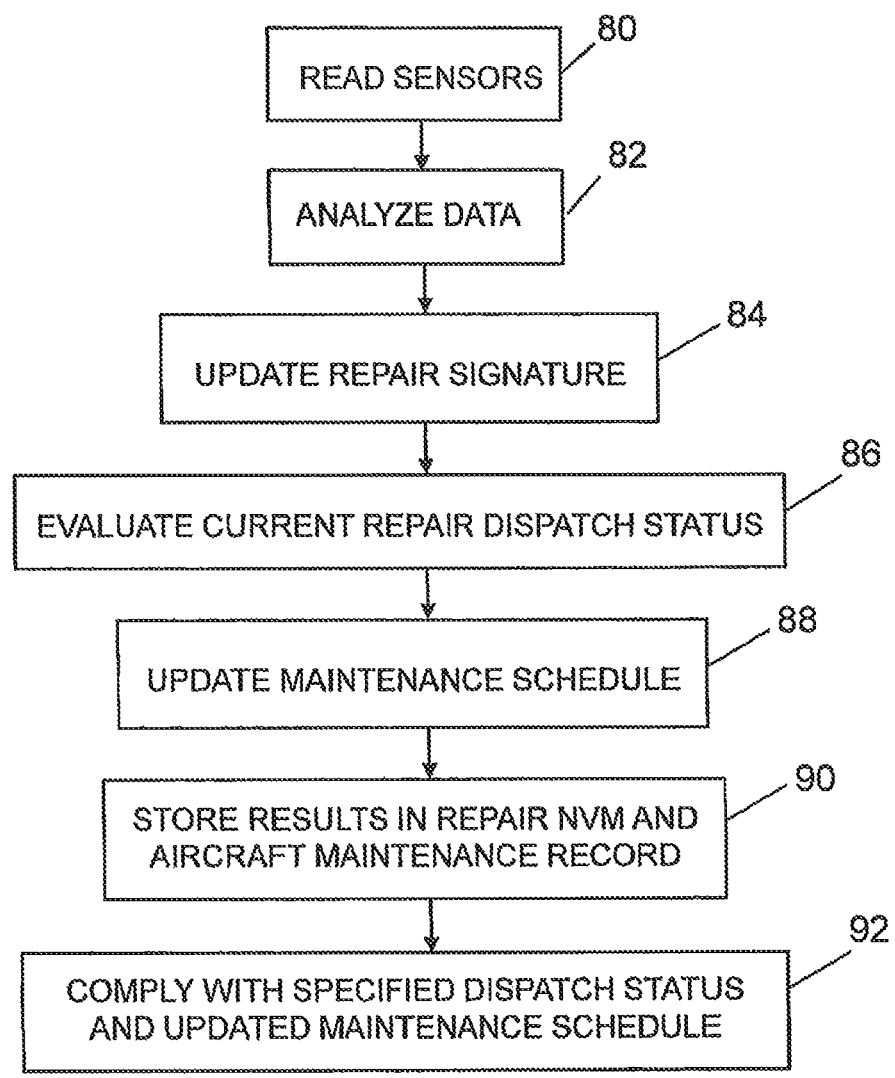
FIG. 8 is a flowchart identifying steps of a process for monitoring the structural integrity of a repair site on a composite structure.

FIG. 8 is a flowchart identifying steps of a process for monitoring the structural integrity of the repair site after the aircraft incorporating the repaired composite structure has been returned to service, exposing the repaired composite structure to loads. During the flight of the aircraft or after the aircraft has landed, the embedded sensors are read (step 80). The acquired sensor data is then analyzed (step 82). Analysis and prognostics are used to provide an updated characterization of the repair (step 84). Then the current repair dispatch status is evaluated (step 86). In light of the state of the repair, i.e., the "repair/bond goodness", an updated schedule of required maintenance of the particular repair is specified (step 88). All results are stored in a repair non-volatile memory and an aircraft maintenance record (steps 90). Thereafter, the operator of the aircraft complies with the specified dispatch status and the updated maintenance schedule (steps 92).

As previously disclosed, the sensors may have many different configurations. For example, each repair patch may incorporate a ply in which a sensor is encapsulated. In accordance with one embodiment, the pressure may be an electrical resistor/conductor whose resistance/conductivity changes as a function of the pressure being exerted on the sensor.

Figure 9:
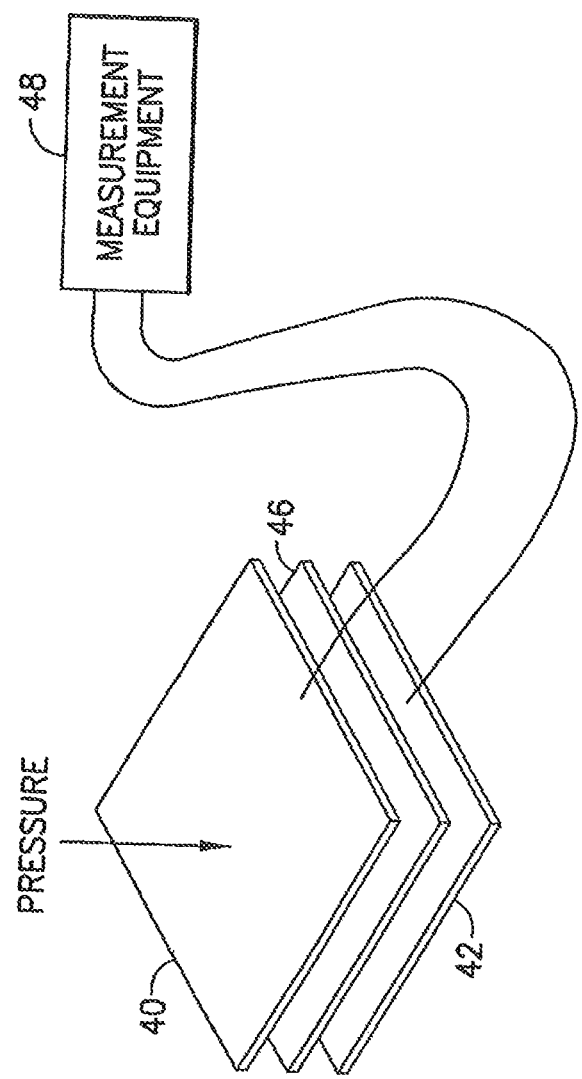
FIG. 9 is a diagram representing an exploded view of components of a system for measuring the electric current flowing through a pressure sensor sandwiched between plies of composite material.

FIG. 9 represents an exploded view of components of a system for measuring pressure with a sensor 46 sandwiched between plies 40 and 42 made of composite material. For example, the electrical resistance of the sensor 46 can be measured using measurement equipment 48 (e.g., an ohmmeter).

Figure 10:
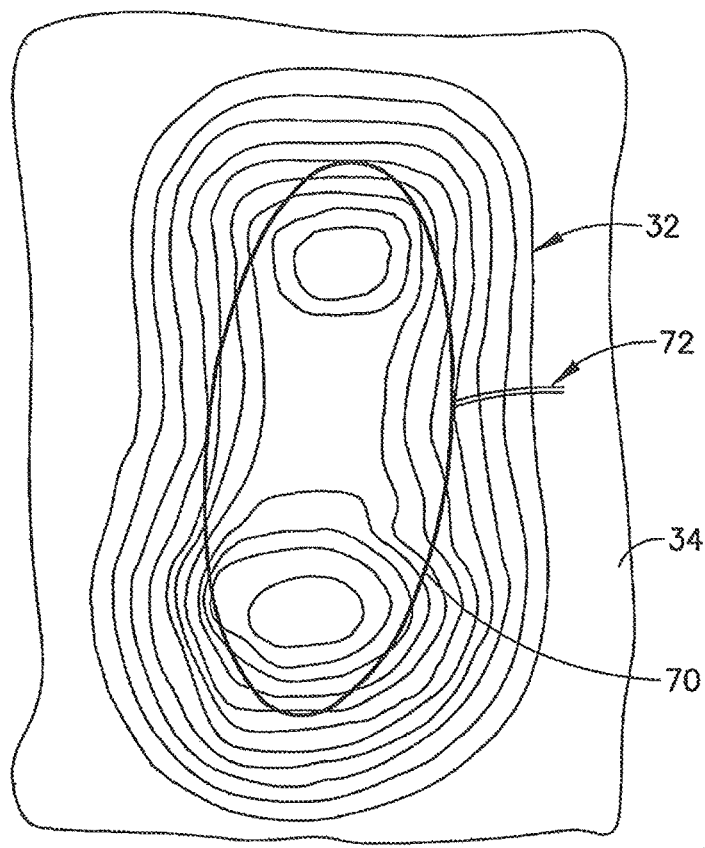
FIG. 10 is a diagram showing a loop-shaped pressure sensor superimposed on a repair site of a composite parent structure in accordance with another embodiment. The repair patch, in which the sensor will be embedded, is not shown in FIG. 10.
Figure 11:
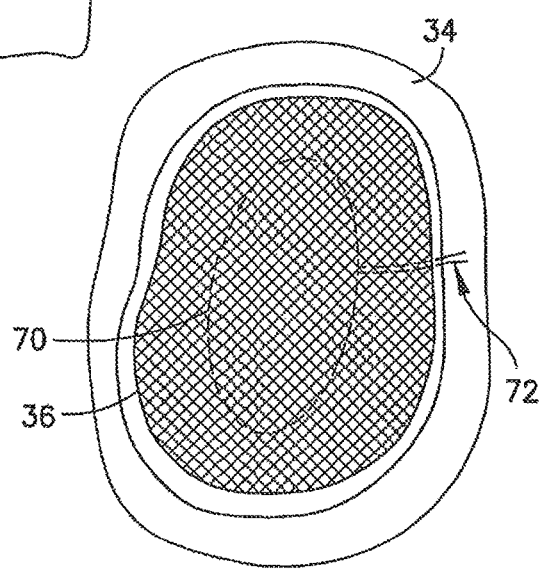
FIG. 11 is a diagram showing the repair site of FIG. 10 after a repair patch has been applied. The dashed ellipse in FIG. 11 indicates the position of the loop-shaped pressure sensor which is embedded in the repair patch and therefore hidden from view.

FIG. 10 represents a loop-shaped sensor 70 superimposed on a repair site 32 of a composite parent structure 34 in accordance with another embodiment. The repair patch, in which the sensor will be embedded, is not shown in FIG. 10. A pair of output terminals are connected to the loop-shaped sensor 70 for data acquisition. FIG. 11 shows the repair site of FIG. 10 after a repair patch 36 has been applied. The dashed ellipse in FIG. 11 indicates the position of the loop-shaped sensor 70 which is embedded in the repair patch 36 and therefore hidden from view. After the composite repair has been cured and sanded, the loop-shaped sensor 70 embedded in the repair will be electrically coupled to a power supply.

The sensor 70 is powered and senses a baseline "goodness or state of the repair". Then after return to service, the repair integrity is periodically monitored/measured and evaluated. Sensor environmental compensation is developed and used to normalize measurements to prevent false evaluations, which is a part of the analysis for DDSA. Significant changes to "goodness or state of the repair" are identified during periodic monitoring sessions and updated signature, dispatch status and maintenance schedule changes are reported.

The composite repair system shown in FIGS. 10 and 11 comprises a loop-shaped sensor 70 which is embedded between plies of the composite repair patch 36. This loop-shaped sensor 70 comprises an electrically conductive structure having an electrical conductivity that varies as a function of the pressure exerted on that structure. For example, the loop-shaped sensor 70 may be fabricated from a material compatible with the composite repair materials and process (e.g., carbon, nanotubes, glass, polymer fiber, silicon, metal foil) or constructed as a microelectromechanical system. If the composite material of the repair patch is cracked or delaminated (see FIGS. 2A-2C), this damage will change the pressure sensed by the embedded sensor relative to a baseline pressure sensor measurements. Sensor compensation factors to correct for environmental differences (e.g., temperature, altitude pressure bias, cabin pressurization) between new measurements and baseline pressure measurements can be documented during testing and applied during the use of DDSA. This would help eliminate measurement errors due to environmental change. Each repair patch on an aircraft can be provided with a respective sensor that is specifically designed to conform to the shape of the repair patch.

Figure 12:
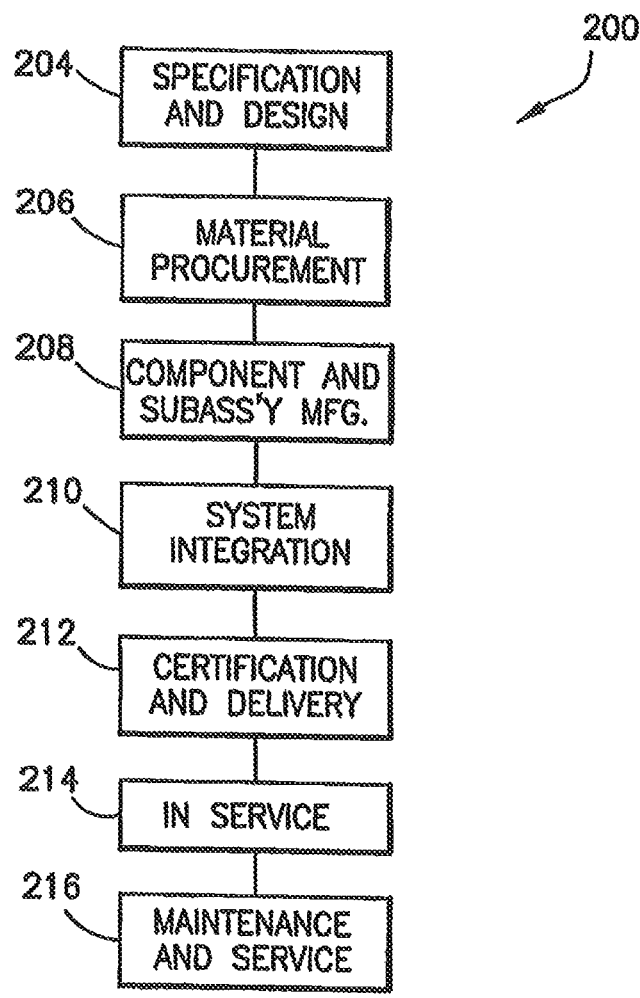
FIG. 12 is a flow diagram of an aircraft production and service methodology.
Figure 13:
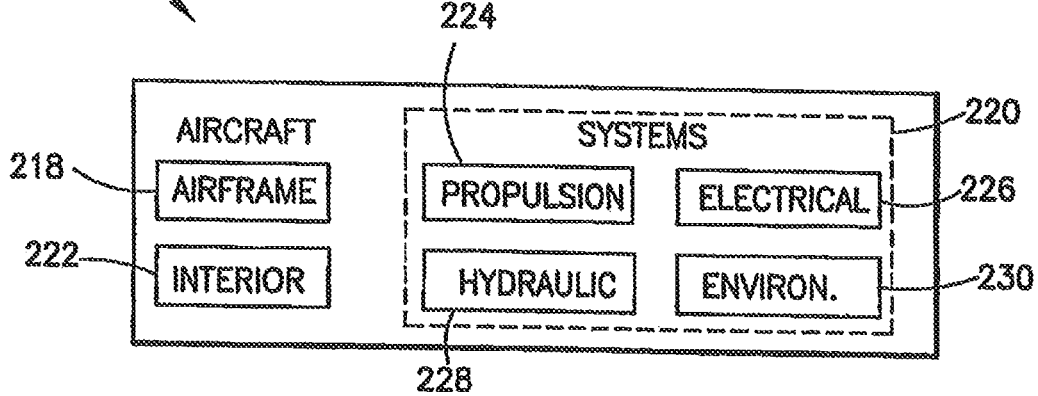
FIG. 13 is a block diagram showing systems of an aircraft.

The monitoring system and process disclosed above may be employed in an aircraft manufacturing and service method 100 as shown in FIG. 12 for assembling and maintaining an aircraft 202 of a type depicted in FIG. 13. During pre-production, exemplary method 200 may include specification and design 204 of the aircraft 202 and material procurement 206. During production, component and subassembly manufacturing 208 and system integration 210 of the aircraft 202 takes place. Thereafter, the aircraft 222 may go through certification and delivery 212 in order to be placed in service 214. While in service by a customer, the aircraft 202 is scheduled for routine maintenance and service 216 (which may also include modification, reconfiguration, refurbishment, and so on). More specifically, routine maintenance and service 216 includes, but is not limited to, repairing damaged composite and monitoring the structural integrity of the repaired component in accordance with contents herein.

Each of the processes of method 200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 13, the aircraft 202 produced by exemplary method 200 may include an airframe 228 with a plurality of systems 220 and an interior 222. Examples of high-level systems 220 include one or more of the following: a propulsion system 224, an electrical system 226, a hydraulic system 228, and an environmental control system 230. Any number of other systems may be included.

The apparatus and processes disclosed herein for monitoring the structural integrity of composite material may be utilized during routine maintenance and service 216 of an aircraft 202.

While various embodiments have been described, it will be understood by those skilled in the art that various changes may be made and equivalents may be substituted for elements thereof without departing from the intended scope. In addition, many modifications may be made to adapt the contents herein to a particular situation without departing from the scope thereof. Therefore it is intended that the claims not be limited to the particular embodiments disclosed.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit.

The method claims set forth hereinafter should not be construed to require that the steps recited therein be performed in alphabetical order or in the order in which they are recited. Nor should they be construed to exclude any portions of two or more steps being performed concurrently or alternatingly.

What is claimed is:

1. A method for verifying electrical connectivity of a repaired component of a parent structure having a composite layer and a conductive layer, the conductive layer having an interwoven wire fabric layer, the method comprising:
   placing a repair patch over a repair site on the component, the repair patch including a plurality of plies of composite material and a ply of conductive material, the ply of conductive material having a patch-interwoven wire fabric layer, wherein the ply of conductive material is configured such that wires in the patch-interwoven wire fabric layer overlap wires in the interwoven wire fabric layer of the conductive layer of the parent structure;
   embedding a sensor in the repair patch, the sensor configured to detect electrical conductivity at the repair site;
   curing the plurality of plies of composite material of the repair patch so that the sensor is bonded to the repair site;
   acquiring a baseline set of sensor data from the sensor which represents an electrical connectivity between the ply of conductive material of the repair patch and the conductive layer of the parent structure;
   acquiring an additional set of sensor data from the sensor at a time subsequent to acquiring the baseline set of sensor data, the additional set of sensor data representing an electrical connectivity between the ply of conductive material of the repair patch and the conductive layer of the parent structure;
   comparing a difference between the baseline set of sensor data and the additional set of sensor data; and
   determining whether the difference between the baseline set of sensor data and the additional set of sensor data exceeds a specified threshold.

2. The method of claim 1, wherein comparing the difference between the baseline set of sensor data and the additional set of sensor data comprises creating a baseline signature based on the baseline set of sensor data, creating an additional signature based on the additional set of sensor data, and comparing the baseline signature and additional signature.

3. The method of claim 1, further comprising issuing an alert signal in response to the difference between the baseline set of data and the additional set of data exceeding the specified threshold.

4. The method of claim 3, wherein issuing the alert signal comprises specifying a maintenance schedule for the repair site.

5. The method of claim 1, further comprising subjecting the parent structure and repair patch to loads, wherein acquiring the baseline set of sensor data occurs prior to subjecting the parent structure and repair patch to loads, and wherein acquiring the additional set of sensor data occurs subsequent to subjecting the parent structure and repair patch to loads.

6. The method of claim 5, wherein the parent structure comprises an aircraft, and wherein subjecting the parent structure and repair patch to loads comprises flying the aircraft.

7. The method of claim 1, wherein placing the repair patch over the repair site comprises positioning the ply of conductive material to have an overlap width relative to the conductive layer of the parent structure.

8. The method of claim 1, wherein the additional set of sensor data is obtained during a flight of the parent structure.

9. A system comprising:
a parent structure having a composite layer and a conductive layer, the conductive layer having an interwoven wire fabric layer, the parent structure defining a repair site;
a repair patch including a plurality of plies of composite material and a ply of conductive material having a patch-interwoven wire fabric layer, the repair patch bonded to the composite layer of the parent structure, such that wires in the patch-interwoven wire fabric layer of the ply of conductive material overlap wires of the interwoven wire fabric layer of the conductive layer of the parent structure; and
a sensor embedded in the repair patch, the sensor configured to detect electrical connectivity between the ply of conductive material of the repair batch and the conductive layer of the parent structure at the repair site.

10. The system of claim 9, further comprising a non-volatile memory embedded in the repair patch and operably coupled to the sensor.

11. The system of claim 9, further comprising an interface unit embedded in the repair patch and operably coupled to the sensor.

12. The system of claim 11, wherein the interface unit comprises a transceiver.

13. The system of claim 9, further comprising a power supply supported by the parent structure and operably coupled to the sensor.

14. The system of claim 9, further comprising a processor programmed to:
receive a baseline set of data from the sensor representing an electrical connectivity between the ply of conductive material of the repair patch and the conductive layer of the parent structure;
acquire an additional set of sensor data from the sensor at a time subsequent to acquiring the baseline set of sensor data, the additional set of sensor data representing an electrical connectivity between the ply of conductive material of the repair patch and the conductive layer of the parent structure;
compare a difference between the baseline set of sensor data and the additional set of sensor data; and
determine whether the difference between the baseline set of sensor data and the additional set of sensor data exceeds a specified threshold.

15. The system of 9, wherein the ply of conductive material of the repair patch is configured to have an overlap width relative to the conductive layer of the parent structure.

16. The system of 15, wherein the overlap width is approximately 1 inch.

17. A method of monitoring a repair site of a parent structure having a plurality of composite layers and a conductive layer, the conductive layer having an interwoven wire fabric layer, the method comprising:
applying a repair patch to the repair site, the repair including a plurality of plies of composite material and a ply of conductive material, the ply of conductive material having a patch-interwoven wire fabric layer, wherein wires of patch-interwoven wire fabric layer of the ply of conductive material overlap wires of the interwoven wire fabric layer of the conductive layer of the parent structure, the repair patch further including at least one sensor configured to detect electrical conductivity at the repair site;
acquiring a baseline set of sensor data from the sensor which represents an electrical connectivity between the ply of conductive material of the repair patch and the conductive layer of the parent structure;
periodically acquiring additional sets of sensor data from the sensor at times subsequent to acquiring the baseline set of sensor data, the additional sets of sensor data representing electrical connectivity between the ply of conductive material of the repair patch and the conductive layer of the parent structure; and
analyzing the periodically acquired sets of sensor data and the baseline set of sensor data to determine an integrity of the electrical connectivity between the ply of conductive material of the repair patch and the conductive layer of the parent structure.

18. The method of claim 17, wherein applying the repair patch to the repair site comprises positioning the ply of conductive material to have an overlap width relative to the conductive layer of the parent structure.

19. The method of claim 17, wherein the overlap width is approximately 1 inch.

20. The method of claim 17, wherein the sensor is embedded in the repair patch along a peripheral region in which the repair patch overlies the parent structure.

* * * * *